United States Patent

Walker et al.

[11] Patent Number: 5,397,346
[45] Date of Patent: Mar. 14, 1995

[54] PROSTHETIC HEART VALVE WITH SEWING RING

[75] Inventors: Charlotte A. Walker; Joseph A. Sauter; Louis A. Campbell, all of Austin, Tex.

[73] Assignee: Carbomedics, Inc., Austin, Tex.

[21] Appl. No.: 875,241

[22] Filed: Apr. 28, 1992

[51] Int. Cl.⁶ .............................................. A61F 2/24
[52] U.S. Cl. .................................................. 623/2
[58] Field of Search ............................................ 623/2

[56] References Cited

U.S. PATENT DOCUMENTS

| | | | |
|---|---|---|---|
| 3,491,376 | 1/1970 | Shiley | 623/2 |
| 3,579,642 | 5/1971 | Heffernan et al. | 623/2 |
| 3,781,969 | 1/1974 | Anderson | 623/2 X |
| 3,997,923 | 12/1976 | Possis | 623/2 |
| 4,535,483 | 8/1985 | Klawitter et al. | 623/2 |
| 4,742,253 | 5/1988 | Magladry | 623/2 |
| 4,935,030 | 6/1990 | Alonso | 623/2 |
| 5,032,128 | 7/1991 | Alonso | 623/2 |
| 5,035,709 | 7/1991 | Wieting et al. | 623/2 |
| 5,071,431 | 12/1991 | Sauter et al. | 623/2 |
| 5,104,406 | 4/1992 | Curcio et al. | 623/2 |
| 5,163,954 | 11/1992 | Curcio et al. | 623/2 |
| 5,178,633 | 1/1993 | Peters | 623/2 |

FOREIGN PATENT DOCUMENTS 0350302  10/1990  European Pat. Off. .

OTHER PUBLICATIONS

Star Tribune (Minneapolis, Minn.) Nov. 9, 1990, 1D.

Primary Examiner—David H. Willse
Assistant Examiner—Mary Beth Jones
Attorney, Agent, or Firm—John R. Merkling

[57] ABSTRACT

A prosthetic mechanical heart valve with a suture ring and stiffening ring combination which minimizes the radial thickness of the sewing ring. The valve comprises an annular stiffening ring captured between upper and lower rings which are sewed into a knit fabric tube. The entire assembly of sewing ring and stiffening ring is then assembled as a unit onto the mechanical heart valve.

9 Claims, 2 Drawing Sheets

PROSTHETIC HEART VALVE WITH SEWING RING

BACKGROUND OF THE INVENTION

Our invention is directed to a prosthetic heart valve with an improved suture ring and to a method for securing the suture ring to the heart valve.

A standard implantable mechanical heart valve usually has an annular valve housing or body to provide a passageway for blood. Leaflets are mounted in the annular body and open or close the blood flow passageway. Usually there are one or two leaflets, but occasionally triple leaflet configurations have been proposed. On the outside of the valve body there is usually a circumferential groove. This groove is used to attach of a suture ring to the valve body.

The suture ring is used to sew the heart valve to the patient's heart tissue. The ring generally comprises a knit fabric tube which is rolled into a toroidal form and which is secured about the heart valve body in the circumferential groove. Various methods and apparatus have been proposed for securing the suture ring to the heart valve. It is known, for instance, to bind the ring into the groove with a plastic thread. It has also been proposed to form a rotatable suture rings on the heart valve using heat shrinkable plastic material, as disclosed in U.S. Pat. No. 3,781,969. U.S. Pat. No. 3,491,376 suggests that a suture ring should be formed as a separate sub-assembly which should then be attached to the heart valve. In the '376 patent, the suture ring is described as including a resilient annular member which is temporarily deformed, so as to snap the ring onto the valve body. U.S. Pat. No. 3,579,642 proposes the use of metal snap rings which must be radially expanded to place the suture ring about the valve body. In such fabrication techniques, however, there is a risk of potential damage to the suture rings when the ring is mechanically expanded to place it about the valve body.

In U.S. Pat. No. 4,743,253, Magladry proposed a two-part suture ring comprising the knit fabric and an internal crescent-shaped ring which would be deformed inwardly by electromagnetic forming to clamp the heart valve while permitting relative rotation between the suture ring and the heart valve.

In U.S. Pat. No. 5,071,431, two of us (Sauter and Campbell) and Poehlmann, disclosed a suture ring comprised of essentially three parts: a stiffening ring which fits over an outer surface of a heart valve; a knit fabric sewing cuff attached to the stiffening ring, and a locking band for securing the stiffening ring to the heart valve.

It has been found that the efficiency of a prosthetic heart valve is most dependent on the size of the valve. In other words, improved hemodynamic characteristics can be expected if the central orifice of the heart valve is made as large as possible with respect to the patient's anatomy. To accomplish this goal, the suture ring assembly, with its associated stiffening ring, should be made as thin radially as possible. In the past, suture ring-stiffening ring combinations have most frequently been made with three metallic components: a central stiffening ring and an upper and lower capture ring to capture the knit fabric tube of the sewing ring. To hold the upper and lower rings in position, the stiffening ring has frequently been formed with grooves to retain the capture rings against an outer side of heart valve annular body. This results in additional radial bulk. To overcome this problem, the assignee of our invention has heretofore attempted to employ spring loaded capture ring to allow the sewing ring to be placed over the stiffening ring after assembly, eliminating the grooves in the stiffening ring. This solution has not been completely satisfactory. There remains a need, therefore, for an improved sewing ring used in conjunction with a stiffening ring to minimize the overall radial thickness of the ring.

SUMMARY OF OUR INVENTION

We have invented a prosthetic heart valve with a suture ring and stiffening ring combination which minimizes the radial thickness of the sewing ring. Our invention comprises an annular stiffening ring captured between upper and lower rings which are sewed into a knit fabric tube. The entire assembly of sewing ring and stiffening ring is then assembled as a unit onto a mechanical heart valve.

The principle object of our invention is to provide an improved prosthetic heart valve having a sewing ring and stiffening ring combination which minimizes the radial thickness thereof.

Other objects and advantages of our invention will become apparent from the following detailed description taken with reference to the accompanying drawings.

DETAILED DESCRIPTION OF OUR PREFERRED EMBODIMENT

Figures 1, 2:
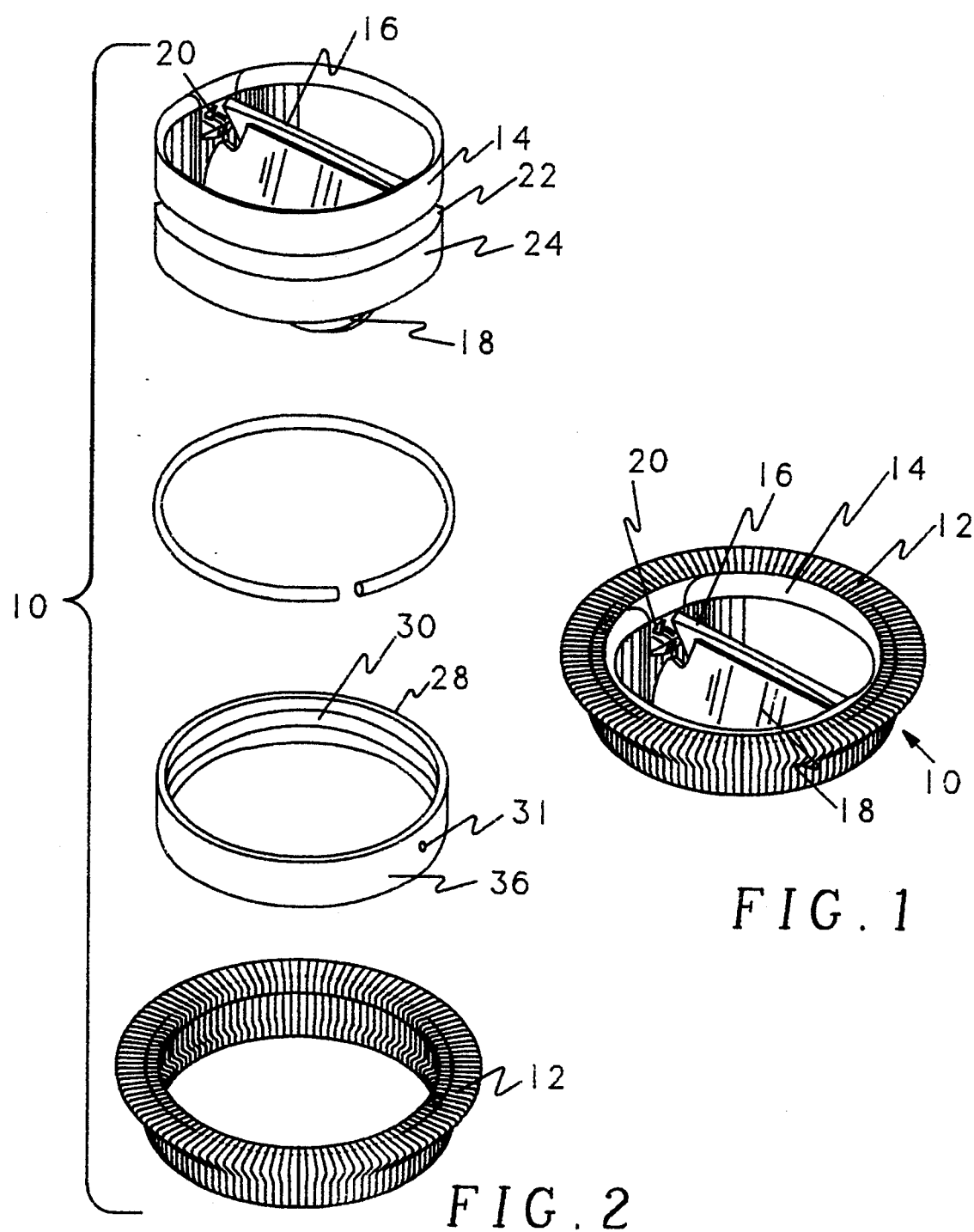
FIG. 1 is a prospective view of a prosthetic mechanical heart valve with a sewing ring.
FIG. 2 is an exploded prospective view of the heart valve of FIG. 1.

We will now describe our preferred embodiment of our invention with reference to the accompanying drawings. In the drawings, like numerals will designate like parts throughout.

FIG. 1 is a prospective view of a prosthetic heart valve, generally designated 10, with a suture ring 12 in accordance with our present invention. The heart valve 10 comprises an annular valve body 14 with pivoting leaflets 16, 18. In the embodiment shown, we have illustrated a bileaflet mechanical heart valve. Single leaflet and multiple leaflet valves could also be used with our invention. The leaflet 18 is shown with a portion cut away to reveal a recess 20. A pivot tab (not shown) engages the recess 20, allowing the leaflet to pivot between open and closed positions. As shown in FIG. 2, the annular valve body 14 has an exterior annular groove 22 on a outer surface 24 of the valve body. This groove 22 receives a lock wire 26. Alternative bands are described in U.S. Pat. No. 5,071,431.

The lock wire 26 attaches a stiffening ring 28 to the annular valve body 14. In our preferred embodiment, the annular valve body consists of pyrolitic carbon. It is a hard, wear-resistant, biocompatible carbon, well suited for the construction of artificial heart valves. The material is also brittle. An exterior stiffening ring such as the ring 28 is frequently used with a carbon valve body. The stiffening ring is comprised of a biocompatible metal such as cobalt-chromium or ELGILOY, a trademark of the Elgiloy Company. We have also used ELGILOY metal in the lock wire 26. The stiffening ring has a circumferential inner groove 30 which, like the exterior groove 22 on the annular valve body, engages the lock wire 26. With the stiffening and suture rings on the valve body, the wire 26 is inserted through a hole 31 in the stiffening ring. A corresponding hole may be cut in the suture ring, or stitching may be completed after the wire has been inserted. The suture ring 12 fits over the stiffening ring, as we will now explain.

Figure 3:
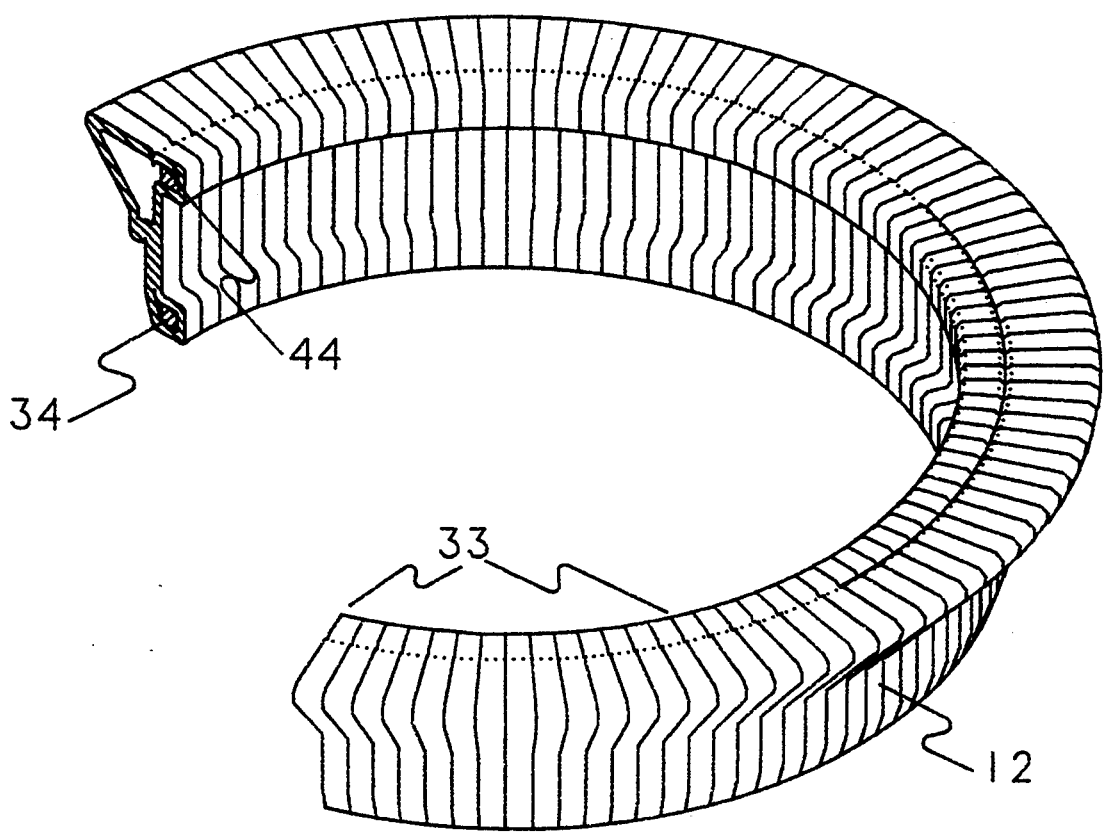
FIG. 3 is a cutaway prospective view of a sewing ring according to our present invention.
Figure 4:
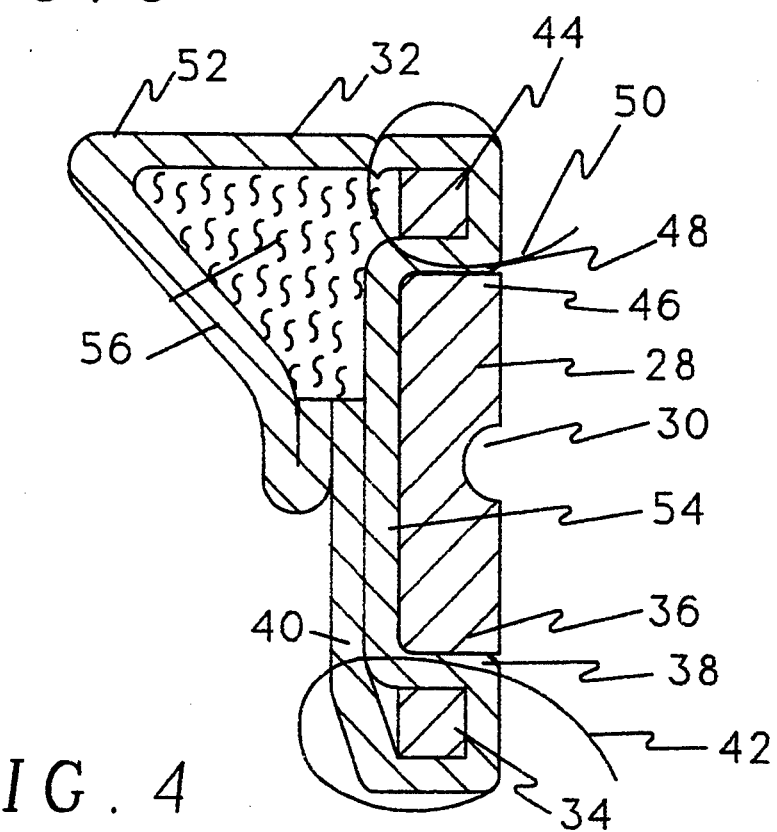
FIG. 4 is a cross sectional view of the sewing ring and stiffening ring combination according to our present invention.

The construction of the suture ring can best be understood by reference to FIGS. 3 and 4. Construction of the suture ring begins with a knit fabric tube 32. DACRON (a trademark) material is a suitable material for such a tube. It is generally knitted with ribs, such as the ribs 33 seen in FIG. 3. The tube 32 has a diameter approximating the outer diameter of the stiffening ring. The stiffening ring 28 is placed within the tube. A lower capture ring 34 is placed on the outside of the tube and pressed up against a lower edge 36 of the stiffening ring. This crimps the tube between the stiffening ring and the lower ring at a bend 38 as seen in FIG. 4. A lower end 40 of the tube is wrapped outwardly around the lower capture ring 34 and the ring is stitched in place. To sew the tube to the lower ring, a continuous thread 32 is passed around the ring. The thread preferably is passed in a clock-wise direction as seen in FIG. 4. The thread 42 is passed between the stiffening ring 28 and the lower ring 34 through the bend 38 in the knit fabric. The stitches may pass from rib to rib, conforming with structure of the knit fabric.

After the lower ring is sewn in place, an upper ring 44 is placed on the outside of the fabric tube and pressed down against an upper end 46 of the stiffening ring 28. As with the lower ring 34 this forms a bend 48 in the knit fabric, which bend is captured between the stiffening ring and the upper ring. As with the lower ring, a continuous stitch is used to sew the upper ring in position. A thread 50 is passed completely around the upper ring 44 in a counter clock-wise direction as seen FIG. 4. The stitches pass over the knit fabric in the region of the upper ring and between the upper ring 44 and the stiffening ring 28 through the bend 48. The upper and lower rings capture the stiffening rings between them. The relative thickness of the sewing ring is reduced because neither the tube nor the upper or lower ring pass beneath any portion of the stiffening ring. To complete the suture ring, an upper end 52 is folded down and the upper end 52 and the lower end 40 of the knit fabric are stitched to a center 54 of the knit fabric, circumferentially along the outside the stiffening ring. The upper end 52 flares away from the stiffening ring to provide an a flange that can be sewn into the tissue at the implantation site. If desired, a filler 56 such as texturized yarn, TEFLON (a trademak) felt, or molded silicon may be captured within the upper end 52.

When the sewing ring and stiffening ring combination has been assembled, it can be attached to the annular valve body by placing the lock wire 26 inside the grooves 22, 30 as described above.

Those skilled in the art will recognize that our invention can be embodied in other specific forms without departing from the spirit or essential characteristics thereof. The foregoing description is intended, therefore, to be in all respects illustrative and not restrictive and the scope of our invention is defined by the following claims. All changes which come within the meaning or equivalency of the claims are intended to be embraced therein.

We claim as our invention:

1. A mechanical heart valve comprising
   an annular valve body,
   an annular stiffening ring circumferentially disposed about said valve body, said stiffening ring having an upper edge and a lower edge,
   an upper ring disposed above said upper edge but not between said stiffening ring and said valve body,
   a lower ring disposed below said lower edge but not between said stiffening ring and said valve body,
   means for non-removably retaining said stiffening ring between said upper and lower rings, said retaining means comprising a fabric tube disposed on the inside of the upper and lower rings and on the outside of the stiffening ring and wherein each of said upper and lower rings are secured to said tube by a thread sewn around each ring and passing between the respective ring and the respective upper or lower edge of said stiffening ring, and
   means attached to said upper and lower edge of said stiffening ring, and
   means attached to said upper and lower rings for suturing said valve into a patient's body.

2. The mechanical heart valve according to claim 1 wherein the stiffening ring and the upper and lower rings each have an outside diameter and wherein the outside diameters of said rings are substantially equal to each other.

3. The mechanical heart valve according to claim 2 further comprising means for securing said stiffening ring to said valve body.

4. The mechanical heart valve according to claim 1 further comprising means for securing said stiffening ring to said valve body.

5. A suture ring for a mechanical heart valve comprising
   an annular stiffening ring adapted to be circumferentially disposed about a valve body, said stiffening ring having an upper edge and a lower edge,
   an upper ring disposed above said upper edge but not between said stiffening ring and said valve body,
   a lower ring disposed below said lower edge but not between said stiffening ring and said valve body,
   means for non-removably retaining said stiffening ring between said upper and lower rings, said retaining means comprising a fabric tube disposed on the inside of the upper and lower rings and on the outside of the stiffening ring and wherein each of said upper and lower rings are secured to said tube by a thread sewn around each ring and passing between the respective ring and the respective upper or lower edge of said stiffening ring, and
   means attached to said upper and lower rings for receiving sutures.

6. The suture ring according to claim 5 wherein the stiffening ring and the upper and lower rings each have an outside diameter and wherein the outside diameters of said rings are substantially equal to each other.

7. A method for assembling a suture ring for a mechanical heart valve comprising the steps of
   placing a fabric tube having upper and lower free ends over an annular stiffening ring,
   placing a fabric tube having upper and lower free ends over an annular stiffening ring, inserting the lower free end of said tube into a lower ring by passing a thread around said ring and between said lower ring and said stiffening ring, securing said lower ring to said tube below a lower edge of said stiffening ring, inserting the upper free end of said tube into an upper ring, securing said upper ring to said tube above an upper edge of said stiffening ring, whereby said stiffening ring is non-removably captured between said upper and lower rings, and attaching said free ends to a central portion of said tube.

8. The method according to claim 7 wherein the step of securing the upper ring comprises passing a thread around said ring and between said upper ring and said stiffening ring.

9. A method for assembling a suture ring for a mechanical heart valve comprising the steps of placing a fabric tube having upper and lower free ends over an annular stiffening ring, inserting the lower free end of said tube into a lower ring, securing said lower ring to said tube below a lower edge of said stiffening ring, inserting the upper free end of said tube into an upper ring, securing said upper ring to said tube above an upper edge of said stiffening ring by passing a thread around said ring and between said upper ring and said stiffening ring, whereby said stiffening ring is non-removably captured between said upper and lower rings, and attaching said free ends to a central portion of said tube.

* * * * *